United States Patent [19]

Jakobson et al.

[11] Patent Number: 5,024,787

[45] Date of Patent: Jun. 18, 1991

[54] PROCESS FOR THE PREPARATION OF FATTY ACID OR HYDROXY FATTY ACID ESTERS OF ISOPROPYLIDENE DERIVATIVES OF POLYGLYCEROLS

[75] Inventors: Gerald Jakobson; Werner Siemanowski, both of Rheinberg; Karl-Heinz Uhlig, Krefeld-Traar, all of Fed. Rep. of Germany

[73] Assignee: Deutsche Solvay-Werke GmbH, Solingen, Fed. Rep. of Germany

[21] Appl. No.: 357,006

[22] Filed: May 25, 1989

[30] Foreign Application Priority Data

May 30, 1988 [DE] Fed. Rep. of Germany ....... 3818292

[51] Int. Cl.$^5$ ............................ C09F 5/08; C09F 7/10
[52] U.S. Cl. .............. 260/410.6; 260/410.7; 549/448; 549/465
[58] Field of Search .......................... 260/410.6, 410.7; 549/448, 465

[56] References Cited

PUBLICATIONS

Chemical Abstracts, vol. 77, p. 397, 1972, :113769r, Prep of Laclylated Monoglycerides.

*Primary Examiner*—Jose G. Dees
*Assistant Examiner*—Deborah D. Carr
*Attorney, Agent, or Firm*—Foley & Lardner

[57] ABSTRACT

A process for the preparation of fatty acid or hydroxy fatty acid esters of isopropylidene derivatives of a polyglycerol involves reacting $C_1$–$C_4$-alkyl esters of $C_6$–$C_{22}$-fatty acids or mono- or polyhydroxy fatty acids in alkaline medium with one or more hydroxyl-containing isopropylidene derivatives of a polyglycerol. The resultant fatty acid or hydroxy fatty acid esters of mono- and/or diisopropylidene derivatives of polyglycerol are useful as intermediates for the preparation of nonionic surfactants, as solvents or solubilizing agents and for cosmetic formulations and skin care preparations.

16 Claims, No Drawings

PROCESS FOR THE PREPARATION OF FATTY ACID OR HYDROXY FATTY ACID ESTERS OF ISOPROPYLIDENE DERIVATIVES OF POLYGLYCEROLS

BACKGROUND OF THE INVENTION

The present invention relates to a process for the preparation of fatty acid or hydroxy fatty acid esters of isopropylidene derivatives of a polyglycerol from $C_1$–$C_4$-alkyl esters of $C_6$–$C_{22}$-fatty acids or mono- or polyhydroxy fatty acids, by reaction in alkaline medium with one or more hydroxyl-containing isopropylidene derivatives of at least one polyglycerol under specific conditions.

It is already known to prepare fatty acid esters, for example tetraesters of polyglycerols, by heating diglycerol for several days with a large excess of fatty acids, for example lauric, palmitic, stearic and oleic acid, in the form of brown, solid or oily compounds (cf. C.A. 41,2392 (1947)). As a result of the long heating, however, only heavily contaminated products can be obtained in very poor yields.

Therefore, an attempt has been made to obtain the corresponding compounds from isopropylidenediglycerol and stearyl-chloride in chloroform. However, the necessary amount of work involved is considerable, since the mixture solidifies after the reaction to yield a paste which after 36 hours has to be taken up in benzene. After the aqueous solution has been separated off and the organic phase washed with water, excess stearic acid must be removed by extraction with 10% strength sodium bicarbonate solution. The organic phase must then be dried over sodium sulfate and the solvent must be distilled off. The resulting residue must be recrystallized twice or several times with alcohols. A further disadvantageous aspect of this process is the fact that hydrochlorides are formed in molar ratios, which either have to be processed further or will represent undesirable impurities in the final product.

OBJECTS OF THE INVENTION

It is therefore an object of the present invention to provide an improved process for the preparation of fatty acid or hydroxy fatty acid esters of an isopropylidene derivative of a polyglycerol.

It is another object of the invention to selectively obtain fatty acid or hydroxy fatty acid esters of an isopropylidene derivative of a polyglycerol in a high yield.

A further object of the invention is to provide an improvement in the process for the preparation of nonionic surfactants where a isopropylidene polyglycerol ester is an intermediate.

Still another object is to provide solvents or solubilizing agents, cosmetic formulations or skin care preparations containing the isopropylidene polyglycerol fatty acid or hydroxy fatty acid esters prepared according to the improved process of the invention.

SUMMARY OF THE INVENTION

These and other objects are achieved by providing a process for preparing fatty acid or hydroxy fatty acid esters of an isopropylidene derivative of a polyglycerol, which comprises the steps of:

(a) reacting a $C_1$–$C_4$-alkyl ester of a $C_6$–$C_{22}$-fatty acid or mono- or polyhydroxy fatty acid, in alkaline medium, with one or more hydroxyl-containing isopropylidene derivatives of a polyglycerol, at a temperature of 140° C.–220° C., and at a pressure of 950–5 mbar, and removing the resultant $C_1$–$C_4$ alcohol by distillation; and (b) recovering the resultant isopropylidene polyglycerol fatty acid or hydroxy fatty acid esters.

Also included as part of the invention is an improvement in a process for preparing nonionic surfactants wherein a isopropylidene polyglycerol ester is an intermediate; the improvement comprising using as the polyglycerol ester the fatty acid or hydroxy fatty acid esters of the mono- and/or diisopropylidene derivatives of polyglycerol prepared by the aforementioned process.

Additionally, the isopropylidene polyglycerol fatty acid or hydroxy fatty acid esters prepared according to the aforementioned process are used as solvents or solubilizing agents, and for cosmetic formulations or skin care preparations.

DETAILED DESCRIPTION OF THE PREFERRED EMBODIMENTS

According to the invention, a process is provided for the preparation of fatty acid or hydroxy fatty acid esters of isopropylidene derivatives of a polyglycerol, in which a $C_1$–$C_4$-alkyl ester of a $C_6$–$C_{22}$-fatty acid or mono- or polyhydroxy fatty acid is reacted in alkaline medium with one or more hydroxyl-containing isopropylidene derivatives of a polyglycerol.

The reaction is carried out at temperatures in the range of about 140° C. to about 220° C., preferably in the range of about 170° C. to about 200° C., and in a vacuum at 950–5 mbar, preferably at 500–10 mbar. The resulting $C_1$–$C_4$ alcohol is removed by distillation, preferably continuously, and the reaction product is purified, preferably by filtration, centrifugation, distillation and/or fractional distillation.

If the reaction is carried out below 140° C., the reaction rates obtained are insufficient, while at temperatures of more than 220° C. a high percentage of undesirable byproducts is formed. On the other hand, if the reaction is carried out at atmospheric pressure, the result is a fairly long reaction time and a higher percentage of undesirable byproducts as well.

Suitable alkyl fatty acid esters include saturated or unsaturated, branched or unbranched alkyl fatty acid esters, which include esters of forerun fatty acids $C_6$–$C_{10}$, lauric acid, myristic acid, coconut fatty acid, stearic acid, behenic acid and/or 2-ethylhexanoic acid, isostearic acid, palm oil fatty acid, oil fatty acid, soya oil fatty acid and/or linoleic acid.

Suitable alkyl hydroxy fatty acid esters include, e.g., ethyl 12-hydroxy stearate, ricinoleic fatty acid ester, and the like.

The hydroxyl-containing isopropylidene derivatives of polyglycerol used are preferably mono- and/or diisopropylidene derivatives of di-, tri- and/or tetraglycerol. It will be appreciated that diisopropylidenediglycerol has no reactive hydroxyls and would not be appropriate for this process.

As the alkaline medium for accelerating the reaction, preferably at least one alkali metal hydroxide and/or alkaline earth metal hydroxide, alkali metal bicarbonate, and alkali metal carbonate and/or alkaline earth metal carbonate, alkali metal alcoholate and/or alkaline earth metal alcoholate, or alkali metal soap and/or alkaline earth metal soap is added.

Preferably, the reaction of the alkyl fatty acid esters, alkyl mono- and/or polyhydroxy fatty acid esters with one or more of the isopropylidene derivatives of a polyglycerol is carried out in the presence of less than 5% by weight of water, preferably less than 1% by weight of water (relative to the total amount of the compounds to be reacted). Accordingly, certain side reactions can be diminished, thereby reducing the amount of impurities which will be present.

According to another preferred embodiment of the process according to the invention, the reaction of the alkyl fatty acid ester, alkyl mono- and/or polyhydroxy fatty acid ester with a mono- and/or diisopropylidene derivative of a di- (with the exception of diisopropylidenediglycerol), tri- and/or tetraglycerol is carried out in a 1.2- to 3-fold, preferably 1.5- to 2.5-fold, molar excess of alkyl fatty acid ester, or alkyl mono- or polyhydroxy fatty acid per hydroxyl group to be reacted (relative to the mono- or diisopropylidene derivatives of the respective polyglycerol). This excess makes it possible to achieve a higher yield.

It is also preferred in the case where a hydroxyl containing mono- and/or diisopropylidene derivative of a di-, tri- and/or tetraglycerol (with the exception of diisopropylidenediglycerol) is reacted with alkyl fatty acid esters, alkyl mono- or polyhydroxy fatty acid esters, that a 2.1-10-fold, preferably 4- to 8-fold, molar excess of monoisopropylidenediglycerol, diisopropylidenetriglycerol and/or diisopropylidenetetraglycerol (relative to the alkyl fatty acid ester, alkyl mono- or polyhydroxy fatty acid ester) be used. By doing so, the amount of monoesters formed is considerably increased.

According to another preferred embodiment, after the reaction of the alkyl fatty acid ester, alkyl mono- or polyhydroxy fatty acid ester, the resulting salts are separated off at a temperature in the range of about 20° C. to about 120° C., preferably in the range of about 40° C. to about 80° C., by any conventional method of filtration.

According to a further preferred embodiment, after the reaction of the alkyl fatty acid ester, alkyl mono- or polyhydroxy fatty acid ester with one or more iso- or diisopropylidene derivatives of di-, tri- and/or tetraglycerol (with the exception of diisopropylidenediglycerol), the excess of the unconverted alkyl fatty acid ester, alkyl mono- or polyhydroxy fatty acid ester and/or the unconverted iso- or diisopropylidene derivatives of di-, tri and/or tetraglycerol are distilled off at reduced pressure, preferably in vacuo, and the remaining reaction product is separated in a conventional manner, preferably by distillation.

The fatty acid or hydroxy fatty acid esters of mono- and/or diisopropylidene derivatives of di-, tri- and/or tetraglycerol prepared according to the invention can be used as intermediates, by acid catalyzed cleavage of the isopropylidene group, for the preparation of non-ionic surfactants.

Furthermore, the fatty acid or hydroxy fatty acid esters (including polyhydroxy fatty acid esters) of mono- and/or diisopropylidene derivatives of di-, tri- and/or tetraglycerol (with the exception of diisopropylidenediglycerol) are used according to the invention as solvents and/or solubilizing agents for lipid-soluble or oil-soluble active compounds, preferably biocides, pharmaceutical active compounds, wood-preservation agents, dyes and paints and/or for cosmetic formulations or skin care preparations.

EXAMPLES

The following examples, which should not be viewed as limiting, are illustrative of the process according to the invention.

1. Reaction of alkyl fatty acid esters with diisopropylidenetriglycerol 1.52 kg (5 mol) methyl oleate and 25 g (0.2 mol) of potassium carbonate are placed in a 4 liter flask and heated with stirring to about 160° C. At a reduced pressure of about 100 mbar, small amounts of water which may be present are distilled off. 820 g (2.5 mol) of diisopropylidenetriglycerol are then added, and the reaction temperature is increased to 180° C.-190° C. At 400-50 mbar, the methanol which is formed is removed by distillation. After a reaction time of 4-5 hours, the mixture is cooled to about 70° C., and precipitated components are filtered off.

Excess alkyl fatty acid ester and unconverted diisopropylidenetriglycerol are removed by distillation at $\leq 0.4$ mbar and a column head temperature of about 160° C. The remaining crude product is then fine-distilled in a short-path evaporation apparatus at $\leq 0.1$ mbar at an oil flow temperature of 210° C.

2. Reaction of alkyl fatty acid esters with monoisopropylidenediglycerol 300 g (about 1 mol) methyl palmitate and 0.5 g of lithium hydroxide monohydrate are placed in a 2 liter flask and heated with stirring to 160° C. At 150 mbar, the water (from the catalyst and that introduced by the fatty acid ester) is removed by distillation.

1.031 kg (5 mol) monoisopropylidenediglycerol are then added, and the reaction temperature is increased to 190° C. At 400-50 mbar (less pressure towards the end of the reaction), the methanol formed is removed by distillation. After a reaction time of 3 hours, the mixture is cooled to 45° C., and precipitated components are filtered off.

Excess monoisopropylidenediglycerol is removed by distillation in a short path evaporation apparatus at $\leq 0.2$ mbar and an oil-flow temperature of about 140° C., the remaining crude product is fine-distilled in the same apparatus at $\leq 0.2$ mbar and an oil-flow temperature of 205° C.

The foregoing description has been set forth merely to describe illustrative embodiments of the invention and is not intended to be limiting. Since modifications of the described embodiments incorporating the spirit may occur to those skilled in the art, the scope of the invention should be limited solely with respect to the appended claims and equivalents.

What is claimed is:

1. A process for preparing fatty acid or hydroxy fatty acid esters of an isopropylidene derivative of a polyglycerol, which comprises the steps of:
   (a) reacting a $C_1$-$C_4$-alkyl ester of a $C_6$-$C_{22}$-fatty acid or mono- or polyhydroxy fatty acid, in alkaline medium, with one or more hydroxyl-containing isopropylidene derivatives of a polyglycerol, at a temperature in the range of about 140° to about 220° C., and at a pressure of 950-5 mbar, and removing the resultant $C_1$-$C_4$ alcohol by distillation; and
   (b) recovering the resultant isopropylidene polyglycerol fatty acid or hydroxy fatty acid esters.

2. The process of claim 1, wherein said reaction temperature is in the range of about 170° C. to about 200° C.

3. The process of claim 1, wherein said reaction pressure is 500-10 mbar.

4. The process of claim 1, wherein said resultant $C_1$-$C_4$ alcohol is removed continuously.

5. The process of claim 1, wherein said resultant isopropylidene polyglycerol fatty acid or hydroxy fatty acid esters are recovered by at least one of filtration, centrifugation, distillation and fractional distillation.

6. The process of claim 1, wherein said alkaline medium comprises at least one alkali metal or alkaline earth metal hydroxide, bicarbonate, carbonate, alcoholate or soap.

7. The process of claim wherein said reaction is carried out in the presence of less than 5% by weight of water, relative to the total amount of the compounds to be reacted.

8. The process of claim 7, wherein said reaction is carried out in the presence of less than 1% by weight of water, relative to the total amount of the compounds to be reacted.

9. The process of claim 1, wherein said hydroxyl-containing isopropylidene derivatives of polyglycerol are at least one of mono- and diisopropylidene derivatives of di-, tri-, and tetraglycerol, diisopropylidenediglycerol being excluded.

10. The process of claim 1, wherein in step (a), said reaction is carried out with a 1.2- to 3-fold excess of said alkyl ester of said fatty acid, or mono- or polyhydroxy fatty acid per hydroxyl group to be reacted, relative to the mono- or diisopropylidene derivatives of said polyglycerol.

11. The process of claim 10, wherein said excess is a 1.5- to 2.5-fold excess.

12. The process of claim 1, wherein in step (a), a hydroxyl-containing mono- or diisopropylidene derivative of di-, tri- or tetraglycerol is reacted with said alkyl ester of a fatty acid or mono- or polyhydroxy fatty acid, and wherein a 2.1- to 10-fold molar excess of monoisopropylidenediglycerol, diisopropylidenetriglycerol or diisopropylidenetriglycerol is used, relative to said alkyl ester.

13. The process of claim 12, wherein a 4- to 8-fold molar excess of said monoisopropylidenediglycerol, diisopropylidenetriglycerol or diisopropylidenetriglycerol is used, relative to said alkyl ester.

14. The process of claim 1, wherein in step (b), said recovery of resultant isopropylidene polyglycerol fatty acid or hydroxy fatty acid esters comprises separating off salts by filtration, at a temperature in the range of about 20° C. to about 120° C.

15. The process of claim 14, wherein said salts are filtered off at a temperature in the range of about 40° C. to about 80° C.

16. The process of claim 1, wherein in step (b), said recovery of resultant isopropylidene polyglycerol fatty acid or hydroxy fatty acid esters comprises distilling off, at reduced pressure, either or both of the unconverted alkyl fatty acid or mono- or polyhydroxy fatty acid ester and the unconverted isopropylidene derivative of diglycerol or diisopropylidene derivative of triglycerol or tetraglycerol.

* * * * *